(12) United States Patent
Köhler et al.

(10) Patent No.: US 6,486,228 B2
(45) Date of Patent: Nov. 26, 2002

(54) MONO-AND BIS-ACYLPHOSPHINE OXIDE PHOTOINITIATOR COMBINATIONS

(75) Inventors: Manfred Köhler, Freiburg (DE); Jean-Pierre Wolf, Maisprach (CH); André Litzler, Spechbach-le-Bas (FR); Guido Tolotti, Saronno (IT); Nils Hoeck, Müllheim (DE)

(73) Assignee: Ciba Specialty Chemicals Corporation, Tarrytown, NY (US)

( * ) Notice: Subject to any disclaimer, the term of this patent is extended or adjusted under 35 U.S.C. 154(b) by 0 days.

(21) Appl. No.: 09/820,105

(22) Filed: Mar. 28, 2001

(65) Prior Publication Data

US 2001/0036978 A1 Nov. 1, 2001

Related U.S. Application Data

(62) Division of application No. 09/453,356, filed on Dec. 1, 1999, now Pat. No. 6,251,963.

(30) Foreign Application Priority Data

Dec. 3, 1998 (CH) ................................................ 2399/98
Mar. 11, 1999 (CH) ................................................ 453/99

(51) Int. Cl.[7] .............................. C08K 3/22; C08F 2/46; C08F 2/50; C08F 4/00; C09D 167/06
(52) U.S. Cl. .............................. 522/64; 522/75; 522/81; 522/83; 522/84; 522/86; 522/107; 522/179; 522/182; 427/570; 427/511; 430/2
(58) Field of Search .......................... 522/64, 81, 83, 522/18, 107, 84, 86, 179, 182, 75; 430/2; 427/570, 511

(56) References Cited

U.S. PATENT DOCUMENTS

| | | | |
|---|---|---|---|
| 4,292,152 A | 9/1981 | Lechtken et al. | 204/159.15 |
| 4,298,738 A | 11/1981 | Lechtken et al. | 546/22 |
| 4,324,744 A | 4/1982 | Lechtken et al. | 260/932 |
| 4,385,109 A | 5/1983 | Lechtken et al. | 430/306 |
| 4,710,523 A | 12/1987 | Lechtken et al. | 522/14 |
| 4,737,593 A | 4/1988 | Ellrich et al. | 568/15 |
| 4,792,632 A | 12/1988 | Ellrich et al. | 568/15 |
| 5,399,770 A | 3/1995 | Leppard et al. | 568/15 |
| 5,472,992 A | 12/1995 | Leppard et al. | 522/18 |

FOREIGN PATENT DOCUMENTS

EP 0446175 9/1991
GB 2292740 3/1996

OTHER PUBLICATIONS

Derwent Abstract 91–269010/37 for EP 0446175.

*Primary Examiner*—Susan W. Berman
(74) *Attorney, Agent, or Firm*—David R. Crichton

(57) ABSTRACT

Photoinitiator combinations comprising at least one compound of formula (I)

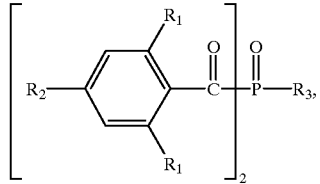

(I)

wherein
$R_1$ is $C_1$–$C_4$alkyl, $C_1$–$C_4$alkoxy or halogen; $R_2$ is hydrogen, $C_1$–$C_4$alkyl, $C_1$–$C_4$alkoxy or halogen; $R_3$ is, for example, $C_1$–$C_{20}$alkyl, cyclopentyl, cyclohexyl, phenyl-$C_1$–$C_4$alkyl, naphthyl or biphenylyl or an O-, S- or N-containing 5- or 6-membered heterocyclic ring; and at least one compound of formula (II)

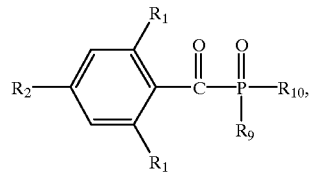

(II)

wherein
$R_1$ and $R_2$ are as defined above; $R_9$ is, for example, $C_1$–$C_{20}$alkyl, cyclopentyl, cyclohexyl, phenyl-$C_1$–$C_4$alkyl, naphthyl, biphenylyl or an O-, S- or N-containing 5- or 6-membered heterocyclic ring; and $R_{10}$ is, for example, $C_1$–$C_{20}$alkyl, $C_2$–$C_{20}$alkyl interrupted by one or more O atoms, cyclopentyl, cyclohexyl, phenyl-$C_1$–$C_4$alkyl, naphthyl, biphenylyl or an O-, S- or N-containing 5- or 6-membered heterocyclic ring; are reactive photohardeners causing only a low degree of yellowing in the cured substrates.

13 Claims, No Drawings

MONO-AND BIS-ACYLPHOSPHINE OXIDE PHOTOINITIATOR COMBINATIONS

This Application is a division of application Ser. No. 09/453,356, filed Dec. 1, 1999, now U.S. Pat. No. 6,251,963.

The invention relates to photoinitiator combinations of mono- and bis-acylphosphine oxides, to compositions comprising those combinations and to their use.

Mono- and bis-acylphosphine oxides are known compounds. For example, monoacylphosphine oxides are described as photoinitiators in U.S. Pat. Nos. 4,298,738, 4,324,744, 4,292,152, 4,385,109 and 4,710,523. Bisacylphosphine oxide compounds are disclosed as photoinitiators in, for example, U.S. Pat. Nos. 4,737,593 and 4,792,632. Alkyl-bisacylphosphine oxides and mixtures of those compounds with α-hydroxyketones or benzophenone compounds are disclosed in U.S. Pat. No. 5,399,770 and U.S. Pat. No. 5,472,992. Further bisacylphosphine oxides are known from GB 2 292 740. EP 446 175 describes mixtures of three components, namely a mono- or bis-acylphosphine oxide, an α-hydroxyketone and a benzophenone.

There is a need in the art for effective photoinitiators that can be incorporated readily and that are capable of curing photopolymerisable compositions effectively, that is to say with good through cure and without extreme yellowing phenomena.

It has now been found that combinations of mono- and bis-acylphosphine oxides meet those requirements in a surprising manner.

The invention therefore relates to photoinitiator combinations comprising (a) at least one compound of formula (I)

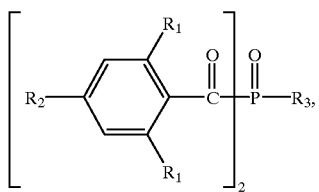

wherein $R_1$ is $C_1$–$C_4$alkyl, $C_1$–$C_4$alkoxy or halogen;

$R_2$ is hydrogen, $C_1$–$C_4$alkyl, $C_1$–$C_4$alkoxy or halogen and $R_3$ is $C_1$–$C_{20}$alkyl, cyclopentyl, cyclohexyl, phenyl-$C_1$–$C_4$alkyl or a group of formula (III)

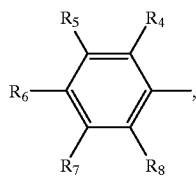

or $R_3$ is naphthyl, biphenylyl or an O-, S- or N-containing 5- or 6-membered heterocyclic ring, the naphthyl, biphenylyl and O-, S- or N-containing 5- or 6-membered heterocyclic ring radicals being unsubstituted or substituted by $C_1$–$C_4$alkyl, $C_1$–$C_4$alkoxy, halogen, $C_1$–$C_4$alkylthio;

$R_4$, $R_5$, $R_6$, $R_7$ and $R_8$ are each independently of the others hydrogen, halogen, $C_1$–$C_{20}$-alkyl, cyclopentyl, cyclohexyl, $C_2$–$C_{12}$alkenyl, $C_2$–$C_{20}$alkyl interrupted by one or more nonconsecutive O atoms, phenyl-$C_1$–$C_4$alkyl, $C_1$–$C_{20}$alkoxy, or phenyl that is unsubstituted or substituted by one or two $C_1$–$C_4$alkyl or/and $C_1$–$C_4$alkoxy substituents; and (b) at least one compound of formula (II)

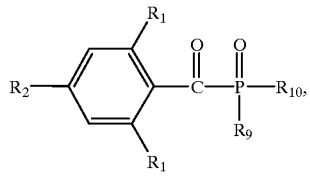

wherein $R_1$ and $R_2$ are as defined above;

$R_9$ is $C_1$–$C_{20}$alkyl, cyclopentyl, cyclohexyl, phenyl-$C_1$–$C_4$alkyl, a group of formula (III), naphthyl, biphenylyl or an O-, S- or N-containing 5- or 6-membered heterocyclic ring, the naphthyl, biphenylyl and O-, S- or N-containing 5- or 6-membered heterocyclic ring radicals being unsubstituted or substituted by $C_1$–$C_4$alkyl, $C_1$–$C_4$alkoxy, halogen, $C_1$–$C_4$-alkylthio; and $R_{10}$ is $C_1$–$C_{20}$alkyl, $C_2$–$C_{20}$alkyl interrupted by one or more non-consecutive O atoms, $C_1$–$C_{20}$alkoxy, cyclopentyl, cyclohexyl, phenyl-$C_1$–$C_4$alkyl, a group of formula (III), naphthyl, biphenylyl or an O-, S- or N-containing 5- or 6-membered heterocyclic ring, the naphthyl, biphenylyl and O-, S- or N-containing 5- or 6-membered heterocyclic ring radicals being unsubstituted or substituted by $C_1$–$C_4$alkyl, $C_1$–$C_4$alkoxy, halogen, $C_1$–$C_4$alkylthio.

$C_1$–$C_{20}$Alkyl is linear or branched and is, for example, $C_1$–$C_{18}$-, $C_1$–$C_{12}$-, $C_1$–$C_8$-, $C_1$–$C_6$- or $C_1$–$C_4$-alkyl. Examples are methyl, ethyl, propyl, isopropyl, n-butyl, sec-butyl, isobutyl, tert-butyl, pentyl, hexyl, heptyl, 2,4,4-trimethyl-pentyl, 2-ethylhexyl, octyl, nonyl, decyl, undecyl, dodecyl, tetradecyl, pentadecyl, hexadecyl, heptadecyl, octadecyl, nonadecyl and eicosyl.

For example, $R_3$ is $C_1$–$C_{18}$alkyl, especially $C_1$–$C_8$alkyl, preferably 2,4,4-trimethylpent-1-yl. $C_1$–$C_4$Alkyl is as defined above up to the corresponding number of carbon atoms. $R_1$ and $R_2$ are preferably methyl.

$C_2$–$C_{20}$Alkyl interrupted one or more times by non-consecutive O atoms is interrupted, for example, from 1 to 9 times, e.g. from 1 to 7 times or once or twice, by O atoms. If the alkyl radical is interrupted by more than one O atom, then the O atoms are each separated from the other(s) by at least one methylene group, yielding, for example, structural units such as —CH$_2$—O—CH$_3$, —CH$_2$CH$_2$—O—CH$_2$CH$_3$, —[CH$_2$CH$_2$O]$_y$—CH$_3$, wherein y=1–9, —(CH$_2$CH$_2$O)$_7$CH$_2$CH$_3$, —CH$_2$—CH(CH$_3$)—O—CH$_2$—CH$_2$CH$_3$ or —CH$_2$—CH(CH$_3$)—O—CH$_2$—CH$_3$, $R_{10}$ may, for example, also be —[OCH$_2$CH$_2$]$_y$—C)CH$_3$, wherein y=1–5, especially wherein y=1, 2 or 3.

$R_{10}$ as $C_2$–$C_{20}$alkyl interrupted one or more times by non-consecutive O atoms may also be, for example, a radical

wherein n is a number from 1 to 4 and m is a number from 1 to 10. The group $C_nH_{2n}$ is accordingly linear or branched $C_1$–$C_4$alkyl. $R_{11}$ is a $C_1$–$C_{20}$alkyl radical. Examples thereof and of $C_1$–$C_4$alkyl are given above. Examples of a radical

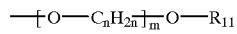

are —$OCH_2CH_2OCH_3$, —$(OCH_2CH_2)_2$—$OCH_3$, —$(OCH_2CH_2)_3$—$OCH_3$, —$(OCH_2CH_2)_4$—$OCM_3$, —$OCM_2CH_2OC_2H_5$, —$(OCH_2CH_2)_2$—$OC_2H_5$, —$(OCH_2CH_2)_3$—$OC_2H_5$, —$(OCH_2CH_2)_4$—$OC_2H_5$, —$OCM_2CH_2OC_3H_7$, —$(OCH_2CH_2)_2$—$OC_3H_7$, —$(OCH_2CH_2)_3$—$OC_3H_7$, —$(OCH_2CH_2)_4$—$OC_3H_7$, —$OCM_2CH_2OC_4H_9$, —$(OCH_2CH_2)_2$—$OC_4H_9$, —$(OCH_2CH_2)_3$—$OC_4H_9$, —$(OCH_2CH_2)_4$—$OC_4H_9$, etc.

$C_1$–$C_{20}$Alkoxy is a linear or branched radical and is, for example, $C_1$–$C_{18}$-, $C_1$–$C_{12}$-, $C_1$–$C_8$-, $C_1$–$C_6$- or $C_1$–$C_4$-alkoxy. Examples are methoxy, ethoxy, propoxy, isopropoxy, n-butyloxy, sec-butyloxy, isobutyloxy, tert-butyloxy, pentyloxy, hexyloxy, heptyloxy, 2,4,4-trimethylpentyloxy, 2-elthylhexyloxy, octyloxy, nonyloxy, decyloxy, dodecyloxy, hexadecyloxy, octadecyloxy and eicosyloxy, especially methoxy, ethoxy, propoxy, isopropoxy, n-butyloxy, sec-butyloxy, isobutyloxy, tert-butyloxy, preferably methoxy.

$C_1$–$C_{12}$Alkoxy, $C_1$–$C_8$alkoxy, $C_1$–$C_6$alkoxy and $C_1$–$C_4$alkoxy are likewise linear or branched and are, for example, as defined above up to the corresponding number of carbon atoms. $R_1$ and $R_2$ are preferably methoxy.

$C_1$–$C_4$Alkylthio is a linear or branched radical and is, for example, methylthio, ethylthio, propylthio, isopropylthio, n-butylthio, sec-butylthio, isobutylthio or tert-butylthio, preferably methylthio.

$C_2$–$C_{12}$Alkenyl radicals may be mono- or poly-unsaturated and linear or branched and are, for example, $C_2$–$C_8$-, $C_2$–$C_6$- or $C_2$–$C_4$-alkenyl. Examples are allyl, methallyl, 1,1-dimethylallyl, 1-butenyl, 2-butenyl, 1,3-pentadienyl, 1-hexenyl, 1-octenyl, decenyl and dodecenyl, especially allyl. $R_4$, $R_5$, $R_6$, $R_7$ and $R_8$ as $C_2$–$C_8$alkenyl are, for example, $C_2$–$C_6$alkenyl, especially $C_2$–$C_4$-alkenyl.

Phenyl-$C_1$–$C_4$alkyl is, for example, phenyl-$C_1$–$C_2$alkyl, such as benzyl, phenylethyl, α-methylbenzyl or α,α-dimethylbenzyl, especially benzyl. Substituted phenyl, naphthyl or biphenylyl or the O-, S- or N-containing 5- or 6-membered heterocyclic radical is mono- to penta-substituted, e.g. mono-, di- or tri-substituted, especially mono- or di-substituted. $C_1$–$C_4$Alkyl, $C_1$–$C_4$alkoxy, $C_1$–$C_4$alkylthio and halogen substituents of those radicals are as defined hereinabove or hereinbelow. Preferred substituents are $C_1$–$C_4$-alkyl, especially methyl and ethyl, and $C_1$–$C_4$alkoxy, especially methoxy.

Halogen is fluorine, chlorine, bromine and iodine, especially chlorine and bromine, preferably chlorine.

$R_3$ as an O-, S- or N-containing 5- or 6-membered heterocyclic ring is, for example, furyl, thienyl, pyrrolyl, oxinyl, dioxinyl or pyridyl. The mentioned heterocyclic radicals may be mono- or poly-substituted. Examples thereof are dimethylpyridyl, dimethylpyrrolyl and methylfuryl.

The term "and/or" is intended to indicate that not only one of the defined alternatives (substituents) but several different defined alternatives (substituents) may be present together, that is to say mixtures, of different alternatives (substituents) may be present. The term "at least one" is intended to indicate "one or more than one", e.g. one or two or three, preferably one or two.

The preparation of the compounds of formulae I and II will be known to a person skilled in the art and is described, for example, in U.S. Pat. Nos. 4,298,738, 4,324,744, 4,292,152, 4,385,109, 4,710,523, U.S. 4,737,593, 4,792,632, U.S. 5,399,770, U.S. 5,472,992 and GB 2 292 740. Some of the compounds of formulae I and II are commercially available.

The preparation of the photoinitiator mixtures according to the invention is carried out, for example, by mixing, grinding, melting or dissolving the individual components, it being possible, for example, for liquid components to be used as solvents for the combination partners in question. It is also possible, however, to mix the components together in an inert solvent.

In the dissolving method the mixtures can be prepared, for example, by dissolving the two components (that is to say at least one compound of formula I and at least one compound of formula II), optionally by heating, in suitable solvents or mixtures of solvents. The photoinitiator mixture can be isolated, for example, by precipitation or by evaporation of the solvent.

Suitable solvents are, for example, aliphatic hydrocarbons, e.g. hexane, pentane, heptane, octane and isomeric mixtures of the said solvents. Also possible, however, is the use of aromatic hydrocarbons, for example xylene or toluene, etc. The use of polar solvents, e.g. linear and cyclic ethers, such as diethyl ether, tetrahydrofuran or dioxane, or other polar solvents, e.g. methyl ethyl ketone, is also possible.

Other suitable solvents are, for example, special-boiling-point benzines having an aromatic content of about 3 to 10%. Those solvents can be mixed, for example, with the polar solvents described above. Further examples of suitable solvent mixtures are mixtures of iso-octane and ethyl acetate, and also water-containing mixtures as already mentioned above, e.g. methyl ethyl ketone and water.

The photoinitiator combinations are advantageously separated from the solution by customary separating procedures, for example filtration. If the solvents used are high-boiling solvents, then when the initiator mixture is filtered off washing is carried out with a low-boiling solvent, e.g. hexane, in order to facilitate drying of the compounds. The initiator mixture is advantageously dried at slightly elevated temperature with the application of a vacuum, especially at 40–50° C. and about 50 mbar.

It is also possible, for example, to obtain the initiator mixtures according to the invention by melting the components and then cooling the melt. In that case, for example, first of all a mixture of the two components is prepared and then melted, but it is also possible to melt each component separately and to mix the compounds together in the molten state, or alternatively one component is melted and the other component is added to the melt. The temperatures are dependent upon the melting points of the components in question and are, for example, about from 100° C. to 200° C.

The photoinitiator mixtures contain, for example, from 2 to 50%, e.g. from 5 to 30%, especially from 5 to 20% or from 10 to 20%, compounds of formula I and from 98 to 50%, e.g. from 95 to 70%, especially from 95 to 80% or from 90 to 80%, compounds of formula II. Further mixtures of interest are those wherein the content of compounds of formula I in the mixture with compounds of formula II is from 10 to 40%.

The constituents of the photoinitiator combination (the compounds of formulae I and II) can also be added separately to the substrate to be cured.

Preference is given to photoinitiator mixtures wherein in the compounds of formulae I and II $R_1$ is $C_1$–$C_4$alkyl or $C_1$–$C_4$alkoxy.

Also of special interest are photoinitiator mixtures wherein in the compounds of formula I $R_3$ is $C_1$–$C_{20}$alkyl or a group of formula III, $R_4$, $R_5$, $R_6$, $R_7$ and $R_8$ are each independently of the others hydrogen, $C_1$–$C_{20}$alkoxy or $C_1$–$C_{20}$-alkyl; and in the compounds of formula II $R_{10}$ is a group of formula III, $C_2$–$C_{12}$alkyl interrupted by one or more non-consecutive O atoms, or $C_1$–$C_{20}$alkoxy, and $R_4$, $R_5$, $R_6$, $R_7$ and $R_8$ are as defined above.

Special mention should also be made of photoinitiator mixtures wherein in the compounds of formula I $R_3$ is a group of formula III, $R_4$, $R_5$, $R_6$, $R_7$ and $R_8$ are each independently of the others hydrogen, $C_1$–$C_{20}$alkoxy or $C_1$–$C_{20}$-alkyl, especially hydrogen; and in the compounds of formula II $R_{10}$ is a group of formula III or $C_1$–$C_4$alkoxy, and $R_4$, $R_5$, $R_6$, $R_7$ and $R_8$ are hydrogen.

Also of special interest are photoinitiator combinations wherein in the compounds of formula I $R_3$ is a group of formula III; and in the compounds of formula II $R_{10}$ is a group of formula III, —OCH$_2$CH$_2$OCH$_3$, —(OCH$_2$CH$_2$)$_2$—OCH$_3$, —(OCH$_2$CH$_2$)$_3$—OCH$_3$ or $C_1$—$C_4$alkoxy;

and $R_4$, $R_5$, $R_6$, $R_7$ and $R_8$ are hydrogen.

Preferred examples of compounds of formula I are bis(2,4,6-trimethylbenzoyl)phenyl-phosphine oxide; bis(2,6-dimethylbenzoyl)-phenyl-phosphine oxide; bis(2,6-dimethoxybenzoyl)phenyl-phosphine oxide; bis(2,6-dichlorobenzoyl)-phenyl-phosphine oxide; bis(2,4,6-trimethylbenzoyl)-2,4,4-trimethylpentyl-phosphine oxide; bis(2,6-dimethylbenzoyl)-2,4,4-trimethylpentyl-phosphine oxide; bis(2,6-dimethoxybenzoyl)-2,4,4-trimethylpentyl-phosphine oxide; bis(2,6-dichlorobenzoyl)-2,4,4-trimethylpentyl-phosphine oxide; bis(2,4,6-trimethylbenzoyl)-2-methoxyphenyl-phosphine oxide; bis(2,6-dimethylbenzoyl)-2-methoxyphenyl-phosphine oxide; bis(2,6-dimethoxybenzoyl)-2-methoxyphenyl-phosphine oxide; bis(2,6-dichlorobenzoyl)-2-methoxyphenyl-phosphine oxide; bis(2,4,6-trimethylbenzyl)-2,4-dimethoxyphenyl-phosphine oxide; bis(2,6-dimethylbenzoyl)-2,4-dimethoxyphenyl-phosphine oxide; bis(2,6-dimethoxybenzoyl)-2,4-dimethoxyphenyl-phosphine oxide; bis(2,6-dichlorobenzoyl)-2,4-dimethoxyphenyl-phosphine oxide; bis(2,4,6-trimethylbenzoyl)-2-methylpropyl-phosphine oxide; bis(2,6-dimethylbenzoyl)-2-methylpropyl-phosphine oxide; bis(2,6-dimethoxybenzoyl)-2-methylpropyl-phosphine oxide; bis(2,6-dichlorobenzoyl)-2-methylpropyl-phosphine oxide; bis(2,4,6-trimethylbenzoyl)-n-octyl-phosphine oxide; bis(2,6-dimethylbenzoyl)-n-octyl-phosphine oxide; bis(2,6-dimethoxybenzoyl)-n-octyl-phosphine oxide; bis(2,6-dichlorobenzoyl)-n-octyl-phosphine oxide; bis(2,4,6-trimethylbenzoyl)-2,4-dipentyloxyphenyl-phosphine oxide; bis(2,6-dimethylbenzoyl)-2,4-dipentyloxyphenyl-phosphine oxide; bis(2,6-dimethoxybenzoyl)-2,4-dipentyloxyphenyl-phosphine oxide; bis(2,6-dichlorobenzoyl)-2,4-dipentyloxyphenyl-phosphine oxide; bis(2,4,6-tri-methylbenzoyl)cyclohexyl-phosphine oxide; bis(2,6-dimethylbenzoyl)-cyclohexyl-phosphine oxide; bis(2,6-dimethoxybenzoyl)cyclohexyl-phosphine oxide; bis(2,6-dichlorobenzoyl)-cyclohexyl-phosphine oxide; bis(2,4,6-trimethylbenzoyl)benzyl-phosphine oxide; bis(2,6-dimethylbenzoyl)benzyl-phosphine oxide; bis(2,6-dimethoxybenzoyl)benzyl-phosphine oxide; and bis(2,6-dichlorobenzoyl)benzyl-phosphine oxide.

Compounds containing 2,4,6-trimethylbenzoyl groups are of special interest.

Special preference is given to bis(2,4,6-trimethylbenzoyl)phenyl-phosphine oxide and bis(2,6-dimethoxybenzoyl)-2,4,4-trimethylpentyl-phosphine oxide.

Examples of compounds of formula II are 2,4,6-trimethylbenzoyl-diphenyl-phosphine oxide; 2,6-dimethylbenzoyl-diphenyl-phosphine oxide; 2,6-dimethoxybenzoyl-diphenyl-phosphine oxide; 2,6-dichlorobenzoyl-diphenyl-phosphine oxide; 2,4,6-trimethylbenzoyl-ethoxy-phenyl-phosphine oxide; 2,6-dimethylbenzoyl-ethoxy-phenyl-phosphine oxide; 2,6-dimethoxybenzoyl-ethoxy-phenyl-phosphine oxide; 2,6-dichlorobenzoyl-ethoxy-phenyl-phosphine oxide; 2,4,6-trimethylbenzoyl-methoxy-phenyl-phosphine oxide; 2,6-dimethylbenzoyl-methoxy-phenyl-phosphine oxide; 2,6-dimethoxy-benzoyl-methoxy-phenyl-phosphine oxide; 2,6-dichlorobenzoyl-methoxy-phenyl-phosphine oxide; 2,4,6-trimethylbenzoyl-bis(4-methoxyphenyl)phosphine oxide; 2,6-dimethylbenzoyl-bis(4-methoxyphenyl) phosphine oxide; 2,6-dimethoxybenzoyl-bis(4-methoxyphenyl)phosphine oxide; 2,6-dichlorobenzoyl-bis(4-methoxyphenyl)phosphine oxide; 2,4,6-trimethylbenzoyl-bis(2-methylpropyl)phosphine oxide; 2,4,6-trimethylbenzoyl-bis(4-pentyloxyphenyl)-phosphine oxide; 2,6-dimethylbenzoyl-bis(4-pentyloxyphenyl) phosphine oxide; 2,6-di-methoxybenzoyl-bis(4-pentyloxyphenyl)phosphine oxide; 2,6-dichlorobenzoyl-bis(4-pentyl-oxyphenyl)phosphine oxide; 2,4,6-trimethylbenzoyl-dicyclohexyl-phosphine oxide; 2,6-di-methylbenzoyl-dicyclohexyl-phosphine oxide; 2,6-dimethoxybenzoyl-dicyclohexyl-phosphine oxide; 2,6-dichlorobenzoyl-dicyclohexyl-phosphine oxide; 2,4,6-trimethylbenzoyl-dibenzyl-phosphine oxide; 2,6-dimethylbenzoyl-dibenzyl-phosphine oxide; 2,6-dimethoxybenzoyl-dibenzyl-phosphine oxide; 2,6-dichlorobenzoyl-dibenzyl-phosphine oxide; 2,4,6-trimethyl-benzoyl-(4-methoxyphenyl)-phenyl-phosphine oxide; 2,6-dimethylbenzoyl-(4-methoxy-phenyl)-phenyl-phosphine oxide; 2,6-dimethoxybenzoyl-(4-methoxyphenyl)-phenyl-phosphine oxide; 2,6-dichlorobenzoyl-(4-methoxyphenyl)-phenyl-phosphine oxide; 2,4,6-trimethyl-benzoyl-(2-methylpropyl)-phenyl-phosphine oxide; 2,4,6-trimethylbenzoyl-(4-pentyl-oxyphenyl)-phenyl-phosphine oxide; 2,6-dimethylbenzoyl-(4-pentyloxyphenyl)-phenyl-phosphine oxide; 2,6-dimethoxybenzoyl-(4-pentyloxyphenyl)-phenyl-phosphine oxide; 2,6-dichlorobenzoyl-(4-pentyloxyphenyl)-phenyl-phosphine oxide; 2,4,6-trimethylbenzoyl-cyclo-hexyl-phenyl-phosphine oxide; 2,6-dimethylbenzoyl-cyclohexyl-phenyl-phosphine oxide; 2,6-dimethoxybenzoyl-cyclohexyl-phenyl-phosphine oxide; 2,6-dichlorobenzoyl-cyclohexyl-phenyl-phosphine oxide; 2,4,6-trimethylbenzoyl-benzyl-phenyl-phosphine oxide; 2,6-dimethylbenzoyl-benzyl-phenyl-phosphine oxide; 2,6-dimethoxybenzoyl-benzyl-phenyl-phosphine oxide; and 2,6-dichlorobenzoyl-benzyl-phenyl-phosphine oxide.

Compounds containing 2,4,6-trimethylbenzoyl radicals are of special interest. Preference is given to 2,4,6-trimethylbenzoyl-diphenyl-phosphine oxide, 2,4,6-trimethylbenzoyl-ethoxy-phenyl-phosphine oxide and 2,4,6-trimethylbenzoyl-methoxy-phenyl-phosphine oxide. Further examples are 2,4,6-trimethylbenzoyl-(1,4-dioxa-pent-1-yl)-phenyl-phosphine oxide, 2,4,6-trimethylbenzoyl-(1,4,7-trioxa-oct-1-yl)-phenyl-phosphine oxide and 2,4,6-trimethyl-benzoyl-(1,4,7,10-tetraoxa-undec-1-yl)-phenyl-phosphine oxide.

Examples of photoinitiator mixtures according to the invention (blends) are 5% bis(2,6-dimethoxybenzoyl)-2,4, 4-trimethylpentyl-phosphine oxide and 95% 2,4,6-trimethylbenzoyl-diphenyl-phosphine oxide; 10% bis(2,6-dimethoxybenzoyl)-2,4,4-trimethyl-pentyl-phosphine oxide and 90% 2,4,6-trimethylbenzoyl-diphenyl-phosphine oxide; 20% bis(2,6-dimethoxybenzoyl)-2,4,4-trimethylpentyl-phosphine oxide and 80% 2,4,6-trimethylbenzoyl-diphenyl-phosphine oxide; 25% bis(2,6-dimethoxybenzoyl)-2,4,4-trimethyl-pentyl-phosphine oxide and 75% 2,4,6-trimethylbenzoyl-diphenyl-phosphine oxide; 5% bis(2,6-dimethoxybenzoyl)-2,4,4-trimethylpentyl-phosphine oxide and 95% 2,4,6-trimethylbenzoyl-ethoxy-phenyl-phosphine oxide; 10% bis(2,6-dimethoxybenzoyl)-2,4,4-trimethylpentyl-phosphine oxide and 90% 2,4,6-trimethylbenzoyl-ethoxy-phenyl-phosphine oxide; 20% bis(2,6-dimethoxybenzoyl)-2,4,4-trimethylpentyl-phosphine oxide and 80% 2,4,6-trimethylbenzoyl-ethoxy-phenyl-phosphine oxide; 25% bis(2,6-dimethoxybenzoyl)-2,4,4-trimethylpentyl-phosphine oxide and 75% 2,4,6-trimethylbenzoyl-ethoxy-phenyl-phosphine oxide; 5% bis(2,4,6-trimethylbenzoyl)-2,4,4-trimethylpentyl-phosphine oxide and 95% 2,4,6-trimethylbenzoyl-diphenyl-phosphine oxide; 10% bis(2,4,6-trimethylbenzoyl)-2,4,4-trimethyl-pentyl-phosphine oxide and 90% 2,4,6-trimethylbenzoyl-diphenyl-phosphine oxide; 20% bis-(2,4,6-trimethylbenzoyl)-2,4,4-trimethylpentyl-phosphine oxide and 80% 2,4,6-trimethyl-benzoyl-diphenyl-phosphine oxide; 25% bis(2,4,6-trimethylbenzoyl)-2,4,4-trimethylpentyl-phosphine oxide and 75% 2,4,6-trimethylbenzoyl-diphenyl-phosphine oxide; 5% bis(2,4,6-trimethylbenzoyl)-2,4,4-trimethylpentyl-phosphine oxide and 95% 2,4,6-trimethylbenzoyl-ethoxy-phenyl-phosphine oxide; 10% bis(2,4,6-trimethylbenzoyl)-2,4,4-trimethylpentyl-phosphine oxide and 90% 2,4,6-trimethylbenzoyl-ethoxy-phenyl-phosphine oxide; 20% bis(2,4,6-trimethylbenzoyl)-2,4,4-trimethylpentyl-phosphine oxide and 80% 2,4,6-trimethylbenzoyl-ethoxy-phenyl-phosphine oxide; 25% bis(2,4,6-trimethylbenzoyl)-2,4,4-trimethylpentyl-phosphine oxide and 75% 2,4,6-trimethylbenzoyl-ethoxy-phenyl-phosphine oxide; 5% bis(2,4,6-trimethylbenzoyl)-phenyl-phosphine oxide and 95% 2,4,6-trimethylbenzoyl-diphenyl-phosphine oxide; 10% bis(2,4,6-trimethylbenzoyl)phenyl-phosphine oxide and 90% 2,4,6-trimethylbenzoyl-diphenyl-phosphine oxide; 20% bis(2,4,6-trimethylbenzoyl)phenyl-phosphine oxide and 80% 2,4,6-trimethylbenzoyl-diphenyl-phosphine oxide; 25% bis(2,4,6-trimethyl-benzoyl)phenyl-phosphine oxide and 75% 2,4,6-trimethylbenzoyl-diphenyl-phosphine oxide; 5% bis(2,4,6-trimethylbenzoyl)phenyl-phosphine oxide and 95% 2,4,6-trimethylbenzoyl-ethoxy-phenyl-phosphine oxide; 10% bis(2,4,6-trimethylbenzoyl)phenyl-phosphine oxide and 90% 2,4,6-trimethylbenzoyl-ethoxy-phenyl-phosphine oxide; 20% bis(2,4,6-trimethyl-benzoyl)phenyl-phosphine oxide and 80% 2,4,6-trimethylbenzoyl-ethoxy-phenyl-phosphine oxide; 25% bis(2,4,6-trimethylbenzoyl)phenyl-phosphine oxide and 75% 2,4,6-trimethyl-benzoyl-ethoxy-phenyl-phosphine oxide.

Of special interest are photoinitiator combinations that are obtained by dissolving bis(2,4,6-trimethylbenzoyl)phenyl-phosphine oxide, bis(2,6-dimethoxybenzoyl)-2,4,4-trimethylpentyl-phosphine oxide or bis(2,4,6-trimethylbenzoyl)-2,4,4-trimethylpentyl-phosphine oxide, especially bis(2,4,6-trimethylbenzoyl)phenyl-phosphine oxide, in a liquid compound of formula II. It is also possible, for example, for more than 2, especially 3, components to be used in the mixture.

The invention relates also to compounds of formula IIa

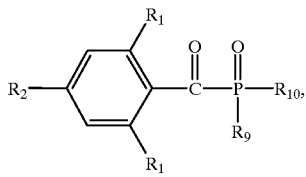

(IIa)

wherein
$R_1$, $R_2$ and $R_9$ are as defined above;
$R_{10}$ is a group

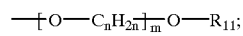

n is a number from 1 to 4;
m is a number from 1 to 10; and
$R_{11}$ is $C_1$–$C_{20}$alkyl.

Preferably n is 2, that is to say an ethylene group is defined. m is, for example, from 1 to 4, especially 1, 2 or 3. The preferred meanings of $R_1$, $R_2$ and $R_9$ are as defined above.

The described compounds of formula IIa fall within the definitions of formula II. In the context of the present description, therefore, all ratios, combinations and compositions described in connection with formula II apply analogously also to the compounds of formula IIa.

According to the invention the photoinitiator combinations described above are used as photoinitiators for the photopolymerisation of ethylenically unsaturated compounds and mixtures comprising such compounds, irradiation being carried out with light in a wavelength range of from 200 to 600 nm. They can be used in this context also in combination with further photoinitiators and/or other additives.

The invention therefore relates also to photopolymerisable compositions comprising
(A) at least one ethylenically unsaturated photopolmerisable compound and
(B) a photoinitiator mixture as described above,
it being possible for the composition to contain, in addition to component (B), also further initiators (C) and/or additives (D).

The unsaturated compounds (A) may contain one or more olefinic double bonds. They may be low molecular weight (monomeric) or higher molecular weight (oligomeric). Examples of monomers having a double bond are alkyl and hydroxyalkyl acrylates and methacrylates, e.g. methyl, ethyl, butyl, 2-ethylhexyl and 2-hydroxyethyl acrylate, isobornyl acrylate and methyl and ethyl methacrylate. Also of interest are silicone acrylates. Further examples are acrylonitrile, acrylamide, methacrylamide, N-substituted (meth)acrylamides, vinyl esters, such as vinyl acetate, vinyl ethers, such as isobutyl vinyl ether, styrene, alkyl- and halo-styrenes, N-vinylpyrrolidone, vinyl chloride and vinylidene chloride.

Examples of monomers having several double bonds are ethylene glycol diacrylate, propylene glycol diacrylate, neopentyl glycol diacrylate, hexamethylene glycol diacrylate and bis-phenol-A diacrylate, 4,4'-bis(2-acryloyloxyethoxy)diphenylpropane, trimethylolpropane triacrylate, pentaerythritol triacrylate and pentaerythritol tetraacrylate, vinyl acrylate, divinyl-benzene, divinyl succinate, diallyl phthalate, triallyl phosphate, triallyl isocyanurate and tris(2-acryloylethyl)isocyanurate.

Examples of higher molecular weight (oligomeric) polyunsaturated compounds are acrylated epoxy resins, acrylated or vinyl-ether- or epoxy-group-containing polyesters, polyurethanes and polyethers. Further examples of unsaturated oligomers are unsaturated polyester resins, which are usually produced from maleic acid, phthalic acid and one or more diols and have molecular weights of about from 500 to 3000. In addition it is also possible to use vinyl ether monomers and oligomers, and also maleate-terminated oligomers having polyester, polyurethane, polyether, polyvinyl ether and epoxide main chains. Combinations of vinyl-ether-group-carrying oligomers and polymers, as described in WO 90/01512, are especially suitable, but copolymers of monomers functionalised with vinyl ether and maleic acid also come into consideration. Such unsaturated oligomers can also be termed prepolymers.

Especially suitable are, for example, esters of ethylenically unsaturated carboxylic acids and polyols or polyepoxides, and polymers having ethylenically unsaturated groups in the chain or in side groups, e.g. unsaturated polyesters, polyamides and polyurethanes and copolymers thereof, polybutadiene and butadiene copolymers, polyisoprene and isoprene copolymers, polymers and copolymers having (meth)acrylic groups in side chains, and also mixtures of one or more such polymers.

Examples of unsaturated carboxylic acids are acrylic acid, methacrylic acid, crotonic acid, itaconic acid, cinnamic acid and unsaturated fatty acids such as linolenic acid or oleic acid. Acrylic and methacrylic acid are preferred.

Suitable polyols are aromatic and especially aliphatic and cycloaliphatic polyols. Examples of aromatic polyols are hydroquinone, 4,4'-dihydroxydiphenyl, 2,2-di(4-hydroxyphenyl)propane, and novolaks and resoles. Examples of polyepoxides are those based on the said polyols, especially the aromatic polyols and epichlorohydrin. Also suitable as polyols are polymers and copolymers that contain hydroxyl groups in the polymer chain or in side groups, e.g. polyvinyl alcohol and copolymers thereof or polymethacrylic acid hydroxyalkyl esters or copolymers thereof. Further suitable polyols are oligoesters having hydroxyl terminal groups.

Examples of aliphatic and cycloaliphatic polyols include alkylenediols having preferably from 2 to 12 carbon atoms, such as ethylene glycol, 1,2- or 1,3-propanediol, 1,2-, 1,3- or 1,4-butanediol, pentanediol, hexanediol, octanediol, dodecanediol, diethylene glycol, triethylene glycol, polyethylene glycols having molecular weights of preferably from 200 to 1500, 1,3-cyclopentanediol, 1,2-, 1,3- or 1,4-cyclohexanediol, 1,4-dihydroxymethylcyclohexane, glycerol, tris(β-hydroxy-ethyl)amine, trimethylolethane, trimethylolpropane, pentaerythritol, dipentaerythritol and sorbitol.

The polyols may be partially or fully esterified by one or by different unsaturated carboxylic acid(s), it being possible for the free hydroxyl groups in partial esters to be modified, for example etherified, or esterified by other carboxylic acids.

Examples of esters are:
trimethylolpropane triacrylate, trimethylolethane triacrylate, trimethylolpropane trimethacrylate, trimethylolethane trimethacrylate, tetramethylene glycol dimethacrylate, triethylene glycol dimethacrylate, tetraethylene glycol diacrylate, pentaerythritol diacrylate, pentaerythritol triacrylate, pentaerythritol tetraacrylate, dipentaerythritol diacrylate, dipentaerythritol triacrylate, dipentaerythritol tetraacrylate, dipentaerythritol pentaacrylate, dipentaerythritol hexaacrylate, tripentaerythritol octaacrylate, pentaerythritol dimethacrylate, pentaerythritol trimethacrylate, dipentaerythritol dimethacrylate, dipentaerythritol tetramethacrylate, tripentaerythritol octamethacrylate, pentaerythritol diitaconate, dipentaerythritol trisitaconate, dipentaerythritol pentaitaconate, dipentaerythritol hexaitaconate, ethylene glycol diacrylate, 1,3-butanediol diacrylate, 1,3-butanediol dimethacrylate, 1,4-butanediol diitaconate, sorbitol triacrylate, sorbitol tetraacrylate, pentaerythritol-modified triacrylate, sorbitol tetramethacrylate, sorbitol pentaacrylate, sorbitol hexaacrylate, oligoester acrylates and methacrylates, glycerol di- and tri-acrylate, 1,4-cyclohexane diacrylate, bisacrylates and bismethacrylates of polyethylene glycol having a molecular weight of from 200 to 1500, and mixtures thereof.

Also suitable as component (A) are the amides of identical or different unsaturated carboxylic acids and aromatic, cycloaliphatic and aliphatic polyamines having preferably from 2 to 6, especially from 2 to 4, amino groups. Examples of such polyamines are ethylenediamine, 1,2- or 1,3-propylenediamine, 1,2-, 1,3- or 1,4-butylenediamine, 1,5-pentylenediamine, 1,6-hexylenediamine, octylenediamine, dodecylenediamine, 1,4-diamino-cyclohexane, isophoronediamine, phenylenediamine, bisphenylenediamine, di-β-aminoethyl ether, diethylenetriamine, triethylenetetramine and di(β-aminoethoxy)- and di(β-aminopropoxy)-ethane. Further suitable polyamines are polymers and copolymers which may have additional amino groups in the side chain and oligoamides having amino terminal groups. Examples of such unsaturated amides are: methylene bisacrylamide, 1,6-hexamethylene bisacrylamide, diethylenetriamine trismethacrylamide, bis(methacrylamidopropoxy)ethane, β-methacrylamidoethyl methacrylate and N-[(β-hydroxyethoxy)ethyl]-acrylamide.

Suitable unsaturated polyesters and polyamides are derived, for example, from maleic acid and diols or diamines. The maleic acid may have been partially replaced by other dicarboxylic acids. They may be used together with ethylenically unsaturated comonomers, e.g. styrene. The polyesters and polyamides may also be derived from dicarboxylic acids and ethylenically unsaturated diols or diamines, especially from those having longer chains of e.g. from 6 to 20 carbon atoms. Examples of polyurethanes are those composed of saturated diisocyanates and unsaturated diols or unsaturated diisocyanates and saturated diols.

Polybutadiene and polyisoprene and copolymers thereof are known. Suitable comonomers include, for example, olefins, such as ethylene, propene, butene and hexene, (meth)acrylates, acrylonitrile, styrene and vinyl chloride. Polymers having (meth)acrylate groups in the side chain are likewise known. Examples are reaction products of novolak-based epoxy resins with (meth)acrylic acid; homo- or co-polymers of vinyl alcohol or hydroxyalkyl derivatives thereof that have been esterified with (meth)acrylic acid; and homo- and co-polymers of (meth)acrylates that have been esterified with hydroxyalkyl (meth)acrylates.

The photopolymerisable compounds can be used on their own or in any desired mixtures. Preferably mixtures of polyol (meth)acrylates are used. Pure acrylate formulations are of special interest.

Binders may also be added to the compositions according to the invention, this being particularly advantageous when the photopolymerisable compounds are liquid or viscous substances. The amount of binder may be, for example, from 5 to 95% by weight, preferably from 10 to 90% by weight and especially from 40 to 90% by weight, based on total solids. The choice of the binder is made in accordance with the field of use and the properties required therefor, such as developability in aqueous and organic solvent systems, adhesion to substrates and sensitivity to oxygen.

Suitable binders are, for example, polymers having a molecular weight of approximately from 5000 to 2 000 000, preferably from 10 000 to 1 000 000. Examples are: homo- and copolymers of acrylates and methacrylates, e.g. copolymers of methyl methacrylate/ethyl acrylate/methacrylic acid, poly(methacrylic acid alkyl esters), poly(acrylic acid alkyl esters); cellulose esters and ethers, such as cellulose acetate, cellulose acetate butyrate, methylcellulose, ethylcellulose; polyvinylbutyral, polyvinylformal, cyclised caoutchouc, polyethers such as polyethylene oxide, polypropylene oxide, polytetrahydrofuran; polystyrene, polycarbonate, polyurethane, chlorinated polyolefins, polyvinyl chloride, copolymers of vinyl chloride/vinylidene chloride, copolymers of vinylidene chloride with acrylonitrile, methyl methacrylate and vinyl acetate, polyvinyl acetate, copoly(ethylene/vinyl acetate), polymers such as polycaprolactam and poly(hexamethylene adipamide), polyesters such as poly(ethylene glycol terephthalate) and poly(hexamethylene glycol succinate).

The unsaturated compounds can also be used in admixture with non-photopolymerisable film-forming components. These may be, for example, polymers that can be dried physically or solutions thereof in organic solvents, for example nitrocellulose or cellulose acetobutyrate, but they may also be chemically or thermally curable resins, for example polyisocyanates, polyepoxides or melamine resins. The concomitant use of thermally curable resins is important for use in so-called hybrid systems, which are photopolymerised in a first step and crosslinked by thermal aftertreatment in a second step.

The photopolymerisable mixtures may also contain various additives (D) in addition to the photoinitiator. Examples thereof are thermal inhibitors, which are intended to prevent premature polymerisation, e.g. hydroquinone, hydroquinone derivatives, p-methoxyphenol, β-naphthol or sterically hindered phenols, e.g. 2,6-di(tert-butyl)-p-cresol. In order to increase dark storage stability it is possible to use, for example, copper compounds, such as copper naphthenate, stearate or octoate, phosphorus compounds, for example triphenylphosphine, tributylphosphine, triethyl phosphite, triphenyl phosphite or tribenzyl phosphite, quaternary ammonium compounds, e.g. tetramethylammonium chloride or trimethylbenzylammonium chloride, or hydroxylamine derivatives, e.g. N-diethylhydroxylamine. For the purpose of excluding atmospheric oxygen during polymerisation it is possible to add paraffin or similar wax-like substances which, being insoluble in the polymer, migrate to the surface at the beginning of the polymersation and form a transparent surface layer which prevents air from entering. Equally possible is the application of a layer that is impermeable to oxygen. As light stabilisers it is possible to add UV absorbers, e.g. those of the hydroxyphenylbenzotriazole, hydroxyphenylbenzophenone, oxalic acid amide or hydroxyphenyl-s-triazine type. Such compounds can be used on their own or in the form of mixtures, with or without the use of sterically hindered amines (HALS).

The following are examples of such UV absorbers and light stabilisers:

1. 2-(2'-Hydroxyphenyl)-benzotriazoles, e.g. 2-(2'-hydroxy-5'-methylphenyl)-benzotriazole, 2-(3',5'-di-tert-butyl-2'-hydroxyphenyl)-benzotriazole, 2-(5'-tert-butyl-2'-hydroxyphenyl)-benzotriazole, 2-(2'-hydroxy-5'-(1,1,3,3-tetramethylbutyl)-phenyl)-benzotriazole, 2-(3',5'-di-tert-butyl-2'-hydroxyphenyl)-5 -chlorobenzotriazole, 2-(3'-tert-butyl-2'-hydroxy-5'-methylphenyl)-5-chlorobenzotriazole, 2-(3'-sec-butyl-5'-tert-butyl-2'-hydroxyphenyl)-benzotriazole, 2-(2'-hydroxy-4'-octyloxyphenyl)-benzotriazole, 2-(3',5'-di-tert-amyl-2'-hydroxyphenyl)-benzotriazole, 2-(3',5'-bis(α,α-dimethylbenzyl)-2'-hydroxyphenyl)benzotriazole, a mixture of 2-(3'-tert-butyl-2 '-hydroxy-5'-(2-octyloxycarbonylethyl)-phenyl)-5-chlorobenzotriazole, 2-(3'-tert-butyl-5'-[2 -(2-ethylhexyloxy)-carbonylethyl]-2'-hydroxyphenyl)-5-chlorobenzotriazole, 2-(3'-tert-butyl-2 '-hydroxy-5'-(2-methoxycarbonylethyl)-phenyl)-5-chlorobenzotriazole, 2-(3'-tert-butyl-2'-hydroxy-5 '-(2-methoxycarbonylethyl)-phenyl)-benzotriazole, 2-(3'-tert-butyl-2'-hydroxy-5'-(2-octyloxycarbonylethyl)-phenyl)-benzotriazole, 2-(3'-tert-butyl-5'-[2-(2-ethylhexyloxy)-carbonylethyl]-2'-hydroxyphenyl)-benzotriazole, 2-(3'-dodecyl-2'-hydroxy-5'-methylphenyl)-benzotriazole and 2-(3'-tert-butyl-2'-hydroxy-5'-(2-isooctyloxycarbonylethyl)-phenyl-benzotriazole, 2,2'-methylene-bis[4-(1,1,3,3-tetramethylbutyl)-6-benzotriazol-2-yl-phenol]; the transesterification product of 2-[3'-tert-butyl-5'-(2-methoxycarbonylethyl)-2'-hydroxyphenyl]-benzotriazole with polyethylene glycol 300; [R—CH$_2$CH$_2$—COO(CH$_2$)$_3$]$_2$— wherein R=3'-tert-butyl-4'-hydroxy-5 '-2H-benzotriazol-2-yl-phenyl.

2. 2-Hydroxybenzophenones, e.g. a 4-hydroxy, 4-methoxy, 4-octyloxy, 4-decyloxy, 4-dodecyloxy, 4-benzyloxy, 4,2', 4'-trihydroxy or 2'-hydroxy-4,4'-dimethoxy derivative.

3. Esters of unsubstituted or substituted benzoic acids, e.g. 4-tert-butyl-phenyl salicylate, phenyl salicylate, octylphenyl salicylate, dibenzoylresorcinol, bis(4-tert-butylbenzoyl)-resorcinol, benzoylresorcinol, 3,5-di-tert-butyl-4-hydroxybenzoic acid 2,4-di-tert-butylphenyl ester, 3,5-di-tert-butyl-4-hydroxybenzoic acid hexadecyl ester, 3,5-di-tert-butyl-4-hydroxy-benzoic acid octadecyl ester and 3,5-di-tert-butyl-4-hydroxybenzoic acid 2-methyl-4,6-di-tert-butylphenyl ester.

4. Acrylates, e.g. (α-cyano-β,β-diphenylacrylic acid ethyl ester or isooctyl ester, α-methoxycarbonylcinnamic acid methyl ester, α-cyano-β-methyl-p-methoxycinnamic acid methyl ester or butyl ester, α-methoxycarbonyl-p-methoxycinnamic acid methyl ester and N-(α-methoxycarbonyl-β-cyanovinyl)-2-methyl-indoline.

5. Sterically hindered amines, e.g. bis(2,2,6,6-tetramethylpiperidyl)sebacate, bis(2,2,6,6-tetramethylpiperidyl)succinate, bis(1,2,2,6,6-pentamethylpiperidyl) sebacate, n-butyl-3,5-di-tert-butyl-4-hydroxybenzylmalonic acid bis(1,2,2,6,6-pentamethylpiperidyl) ester, the condensation product of 1-hydroxyethyl-2,2,6,6-tetramethyl-4-hydroxypiperidine and succinic acid, the condensation product of N,N'-bis(2,2,6,6-tetramethyl-4-piperidyl)hexamethylene-diamine and 4-tert-octylamino-2,6-dichloro-1,3,5-s-triazine, tris(2,2,6,6-tetramethyl-4-piperidyl)nitrilotriacetate, tetrakis(2,2,6,6-tetramethyl-4-piperidyl)-1,2,3,4-butanetetraoate, 1,1'-(1, 2-ethanediyl)-bis(3,3,5,5-tetramethylpiperazinone), 4-benzoyl-2,2,6,6-tetramethylpiperidine, 4-stearyloxy-2,2,6,6-tetramethylpiperidine, bis(1,2,2,6,6-pentamethylpiperidyl)-2-n-butyl-2 -(2-hydroxy-3,5-di-tert-butylbenzyl)-malonate, 3-n-octyl-7,7,9,9-tetramethyl-1,3,8-tri-azaspiro[4.5 ]decane-2,4-dione, bis(1-octyloxy-2,2,6,6-tetramethylpiperidyl)sebacate, bis(1-octyloxy-2,2,6,6-tetramethylpiperidyl)succinate, the condensation product of N,N'-bis(2,2,6,6-tetramethyl-4-piperidyl) hexamethylenediamine and 4-morpholino-2,6- dichloro-1,3,5-triazine, the condensation product of 2-chloro-4,6-di(4-n-butylamino-2,2,6,6-tetramethylpiperidyl)-1,3, 5-triazine and 1,2-bis(3-aminopropylamino)ethane, the condensation product of 2-chloro-4,6-di(4-n-butylamino-1,2,2,6,6-pentamethylpiperidyl)-1,3,5-triazine and 1,2-bis(3-amino-propylamino)ethane, 8-acetyl-3-dodecyl-7,7,9,9-tetramethyl-1,3,8-triazaspiro[4.5]decane-2,4-dione, 3-dodecyl-1-(2,2,6,6-tetramethyl-4-piperidyl)-pyrrolidine-2,5-dione and 3-dodecyl-1-(1,2,2,6,6-pentamethyl-4-piperidyl)-pyrrolidine-2,5-dione.

6. Oxalic acid diamides, e.g. 4,4'-dioctyloxy-oxanilide, 2,2'-diethoxy-oxanilide, 2,2'-dioctyloxy-5, 5'-di-tert-butyl oxanilide, 2,2'-didodecyloxy-5,5'-di-tert-butyl oxanilide, 2-ethoxy-2'-ethyl oxanilide, N,N'-bis(3-dimethylaminopropyl)oxalamide, 2-ethoxy-5-tert-butyl-2'-ethyl oxanilide and a mixture thereof with 2-ethoxy-2'-ethyl-5,4'-di-tert-butyl oxanilide and mixtures of o- and p-methoxy- and of o- and p-ethoxy-disubstituted oxanilides.

7. 2-(2-Hydroxyphenyl)-1,3,5-triazines, e.g. 2,4,6-tris(2-hydroxy-4-octyloxyphenyl)-1,3,5-triazine, 2-(2-hydroxy-4-octyloxyphenyl)-4,6-bis(2,4-dimethylphenyl)-1,3,5-triazine, 2-(2,4-dihydroxyphenyl)-4, 6-bis(2,4-dimethylphenyl)-1,3,5-triazine, 2,4-bis(2-hydroxy-4-propyloxyphenyl)-6-(2,4-dimethylphenyl)-1,3,5-triazine, 2-(2-hydroxy-4-octyloxyphenyl)-4,6-bis(4-methylphenyl)-1,3,5-triazine, 2-(2-hydroxy-4-dodecyloxyphenyl)-4,6-bis(2,4-dimethylphenyl)-1,3,5-triazine, 2-phenyl)-1,3,5-triazine, 2-[2-hydroxy-4-(2-hydroxy-3-octyloxy-propyloxy)-phenyl]-4,6-bis(2,4-dimethylphenyl)-1,3,5-triazine and 2-[4-dodecyloxy/tridecyloxy-(2-hydroxypropyl)oxy-2-hydroxy-phenyl]-4, 6-bis(2,4-dimethylphenyl)-1,3,5-triazine.

8. Phosphites and phosphonites, e.g. triphenyl phosphite, diphenylalkyl phosphites, phenyldialkyl phosphites, tris (nonylphenyl)phosphite, trilauryl phosphite, trioctadecyl phosphite, distearyl-pentaerythritol diphosphite, tris(2,4-di-tert-butylphenyl)phosphite, diisodecylpentaerythritol diphosphite, bis(2,4-di-tert-butylphenyl)pentaerythritol diphosphite, bis(2,6-di-tert-butyl-4-methylphenyl) pentaerythritol diphosphite, bis-isodecyloxy-pentaerythritol diphosphite, bis(2,4-di-tert-butyl-6-methylphenyl)pentaerythritol diphosphite, bis(2,4,6-tri-tert-butylphenyl)-pentaerythritol diphosphite, tristearyl sorbitol triphosphite, tetrakis(2,4-di-tert-butylphenyl)-4,4'-biphenylene diphosphonite, 6-isooctyloxy-2,4,8,10-tetra-tert-butyl-12H-dibenzo[d,g]-1,3, 2-dioxaphosphocine, 6-fluoro-2,4,8,10-tetra-tert-butyl-12-methyl-dibenzo[d,g]-1,3,2-dioxaphosphocine, bis(2,4-di-tert-butyl-6-methylphenyl)methyl phosphite and bis(2, 4-di-tert-butyl-6-methylphenyl) ethyl phosphite.

The invention therefore relates also to photopolymerisable compositions comprising as component (D) UV absorbers from the class of the hydroxyphenyl-s-triazines, hydroxyphenyl-benzotriazoles and sterically hindered amines based on 2,2,6,6-tetramethylpiperidines and/or a pigment, especially a white pigment.

Preference is given to a composition comprising as component (B) a photoinitiator combination comprising bis(2, 4,6-trimethylbenzoyl)phenyl-phosphine oxide, bis(2,6-dimethoxy-benzoyl)-2,4,4-trimethylpentyl-phosphine oxide or bis(2,4,6-trimethylbenzoyl)-2,4,4-tri-methylpentyl-phosphine oxide, especially bis(2,4,6-trimethylbenzoyl) phenyl-phosphine oxide, and compounds of formula II, especially 2,4,6-trimethylbenzoyl-diphenyl-phosphine oxide or 2,4,6-trimethylbenzoyl-ethoxy-phenyl-phosphine oxide. Such compositions contain as component (A) especially acrylates, preferably pure acrylate systems.

In order to accelerate the photopolymerisation it is possible to add amines, e.g. triethanolamine, N-methyl-diethanolamine, p-dimethylaminobenzoic acid ethyl ester or Michler's ketone. The action of the amines can be enhanced by the addition of aromatic ketones of the benzophenone type. Amines suitable for use as oxygen capture agents are, for example, substituted N,N-dialkylanilines, as described in EP 339 841. Further accelerators, co-initiators and auto-oxidisers are thiols, thioethers, disulfides and phosphines, as described e.g. in EP 438 123 and GB 2 180 358.

Photopolymerisation can also be accelerated by the addition of photosensitisers that shift or broaden the spectral sensitivity. These include especially aromatic carbonyl compounds, e.g. benzophenone, thioxanthone, anthraquinone and 3-acylcoumarin derivatives and 3-(aroylmethylene)-thiazolines, and also eosin, rhodamine and erythrosine dyes.

The curing process, especially in the case of pigmented compositions (e.g. compositions pigmented with titanium dioxide), may also be assisted by the addition of a component that forms free radicals under thermal conditions, e.g. an azo compound, such as 2,2'-azobis(4-methoxy-2,4-dimethylvaleronitrile), a triazene, diazosulfide, pentazadiene or a peroxy compound, for example a hydroperoxide or peroxycarbonate, e.g. tert-butyl hydroperoxide, as described e.g. in EP 245 639.

The compositions according to the invention may also comprise a photoreducible dye, e.g. a xanthene, benzoxanthene, benzothioxanthene, thiazine, pyronin, porphyrin or acridine dye, and/or a radiation-cleavable trihalomethyl compound. Similar materials are described, for example, in EFP 445 624.

Further customary additives are—depending upon the intended use—optical brighteners, fillers, pigments, colourants, wetting agents or flow control agents.

The formulations may also contain colourants and/or white or coloured pigments. Depending upon the intended use, both inorganic and organic pigments may be used, special preference being given to white pigments, e.g. titanium dioxide, especially of the rutile type. Such additives will be known to the person skilled in the art; some examples are titanium dioxide pigments, e.g. of the rutile or anatase type, carbon black, zinc oxide, such as zinc white, iron oxides, such as iron oxide yellow, iron oxide red, chromium yellow, chromium green, nickel titanium yellow, ultramarine blue, cobalt blue, bismuth vanadate, cadmium yellow and cadmium red. Examples of organic pigments are mono- or bis-azo pigments, and also metal complexes thereof, phthalocyanine pigments, polycyclic pigments, e.g. perylene, anthraquinone, thioindigo, quinacridone or triphenylmethane pigments, and also diketo-pyrrolo-pyrrole, isoindolinone, e.g. tetrachloroisoindolinone, isoindoline, dioxazine, benzimidazolone and quinophthalone pigments. The pigments may be used in the formulations on their own or in admixture. Depending upon the intended use, the pigments are added to the formulations in amounts customary in the art, for example in an amount of from 1 to 60% by weight, or 10 to 30% by weight, based on the total mass.

The formulations may also comprise, for example, organic colourants of an extremely wide variety of classes. Examples are azo dyes, methine dyes, anthraquinone dyes and metal complex dyes. These too are used in the concentrations customary in the art and known to the person skilled in the art, for example from 0.1 to 20%, especially from 1 to 5%, based on the total mass.

The addition of glass microbeads or pulverised glass fibres, as described, for example, in U.S. Pat. No. 5,013,768, is suitable for the curing of thick and pigmented coatings.

The invention relates also to compositions comprising as component (A) at least one ethylenically unsaturated photopolymerisable compound dissolved or emulsified in water.

Such aqueous radiation-curable prepolymer dispersions are commercially available in many variations and are to be understood as being dispersions consisting of water and at least one prepolymer dispersed therein. The concentration of water in such systems is, for example, from 5 to 80%/c by weight, especially from 30 to 60% by weight. The radiation-curable prepolymer or mixture of prepolymers is present, for example, in concentrations of from 95 to 20% by weighty, especially from 70 to 40% by weight. In such compositions the sum of the percentages mentioned for water and prepolymer will be 100 in each case, the auxiliaries and additives, which will be present in varying amounts in accordance with the intended use, being in addition thereto.

The radiation-curable film-forming prepolymers, which are dispersed or in many cases dissolved in water, are mono- or poly-functional ethylenically unsaturated prepolymers that can be initiated by free radicals, which prepolymers are known per se for aqueous prepolymer dispersions and contain, for example, from 0.01 to 1.0 mol of polymerisable double bonds per 100 g of prepolymer and have an average molecular weight of, for example, at least 400, especially of from 500 to 10 000. Prepolymers having higher molecular weights may also be suitable, however, depending upon the intended use.

There are used, for example, polymerisable C—C double-bond-containing polyesters having an acid number of a maximum of 10, polymerisable C—C double-bond-containing polyethers, hydroxyl-group-containing reaction products of a polyepoxide containing at least two epoxy groups per molecule with at least one $\alpha,\beta$-ethylenically unsaturated carboxylic acid, polyurethane (meth)acrylates and acrylic copolymers containing $\alpha,\beta$-ethylenically-unsaturated acrylic radicals, as described in EP 12 339. Mixtures of those prepolymers may also be used. Also suitable are the polymerisable prepolymers described in EP 33 896, which are thioether adducts of polymerisable prepolymers having an average molecular weight of at least 600, a carboxyl group content of from 0.2 to 15% and a content of from 0.01 to 0.8 mol of polymerisable C—C double bonds per 100 g of prepolymer. Other suitable aqueous dispersions based on specific (meth)acrylic acid alkyl ester polymerisation products are described in EP 41 125, and suitable water-dispersible radiation-curable prepolymers of urethane acrylates can be found in DE 2 936 039.

As further additives the radiation-curable aqueous prepolymer dispersions may comprise dispersing agents, emulsifiers, anti-oxidants, light stabilisers, colourants, pigments, fillers, e.g. talcum, gypsum, silicic acid, rutile, carbon black, zinc oxide, iron oxides, reaction accelerators, flow agents, glidants, wetting agents, thickeners, dulling agents, antifoams and other adjuvants customary in surface-coating technology. Suitable dispersing agents include water-soluble high molecular weight organic compounds having polar groups, e.g. polyvinyl alcohols, polyvinylpyrrolidone and cellulose ethers. As emulsifiers it is possible to use non-ionic and, where appropriate, also ionic emulsifiers.

The photopolymerisable compositions contain the photoinitiator combination (B) advantageously in an amount of from 0.05 to 15% by weight, preferably from 0.1 to 5% by weight, based on the composition. The values indicated relate to the total amount of all photoinitiators present in the composition. If, therefore, further photoinitiators (C) are present in the composition, they are included in the amount indicated above.

The additional additives (D) are used in the amounts customary in the art. These are governed by the use in question and will be familiar to a person skilled in the art.

In certain cases it may be advantageous to use, in addition to the photoinitiator combinations according to the invention, further initiators (C), e.g. benzophenone, benzophenone derivatives, acetophenone, acetophenone derivatives, e.g. $\alpha$-hydroxycycloalkylphenyl ketones, phenyl glyoxalates, dialkoxyacetophenone, $\alpha$-hydroxyacetophenones or $\alpha$-aminoacetophenones, 4-aroyl-1,3-dioxolanes, benzoin alkyl ethers and benzil ketals, camphorquinones, further mono- or bis-acylphosphine oxides or sulfides or trisacylphosphine oxides, titanocenes or ferrocenes. Examples of especially suitable additional photoinitiators are: 1-(4-dodecylbenzoyl)-1-hydroxy-1-methyl-ethane, 1-(4-isopropylbenzoyl)-1-hydroxy-1-methyl-ethane, 1-benzoyl-1-hydroxy-1-methyl-ethane, 1-[4-(2-hydroxyethoxy)-benzoyl]-1-hydroxy-1-methyl-ethane, 1-[4-(acryloyloxyethoxy)-benzoyl]-1-hydroxy-1-methyl-ethane, diphenyl-ketone, phenyl-1-hydroxy-cyclohexyl ketone, (4-morpholinobenzoyl)-1-benzyl-1-dimethyl-amino-propane, 1-(3,4-dimethoxyphenyl)-2-benzyl-2-dimethylamino-butan-1-one, (4-methyl-thiobenzoyl)-1-methyl-1-morpholino-ethane, benzil dimethyl ketal, bis (cyclopentadienyl)-bis(2, 6-difluoro-3-pyrryl-phenyl) titanium, cyclopentadienylarene-iron(II) complex salts, e.g. ($\eta^6$-isopropylbenzene)($\eta^5$-cyclopentadienyl)iron(II) hexafluorophosphate. Further suitable additional photoinitiators can be found in U.S. Pat. No. 4,950,581 column 20, line 35 to column 21, line 35.

Also suitable are triazine compounds, such as the triazines described in EP 137 452, DE 2 718 254 and DE 2 243 621. Further suitable triazines can be found in U.S. Pat. No. 4,950,581, column 14, line 60 to column 18, line 44. Trihalomethyltriazines, such as 2,4-bis(trichloromethyl)-6-(4-styryl-phenyl)-s-triazine, are of special interest.

Where the photoinitiator combinations according to the invention are used in hybrid systems there are used in addition to the free-radical hardeners according to the invention cationic photoinitiators, such as peroxide compounds, e.g. benzoyl peroxide (further suitable peroxides are described in U.S. Pat. No. 4,950,581 column 19, lines 17–25), aromatic sulfonium, phosphonium or iodonium salts (as described e.g. in U.S. Pat. No. 4,950,581 column 18, line 60 to column 19, line 10) or cyclopentadienylarene-iron(II) complex salts, e.g. ($\eta^6$-isopropylbenzene)-($\eta^5$-cyclopentadienyl)iron(II) hexafluorophosphate, oximesulfonates, as described, e.g. in EP 780 729 or EP 571 330, or disulfones or imidosulfonates, e.g.

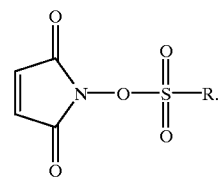

Of special interest are compositions comprising as additional photoinitiators (C) titanocenes, ferrocenes, benzophenones and derivatives thereof, benzoin alkyl ethers, benzil ketals, 4-aroyl-1,3-dioxolanes, dialkoxyacetophenones, α-hydroxyacetophenones or α-aminoacetophenones, α-hydroxycycloalkyl-phenyl ketones, phenylglyoxalic acid esters or derivatives thereof, xanthones, thioxanthones, anthraquinones.

The photopolymerisable compositions may be used for a variety of purposes, for example as printing inks, e.g. for screen printing, offset printing and flexographic printing, as clear lacquers, as white surface-coating compositions, for example for wood or metal, as coating materials inter alia for paper, wood, metal or plastics, as daylight-curable paints for marking structures and roads, for photographic reproduction processes, for holographic recording materials, for image-recording processes or the production of printing plates that can be developed using organic solvents or using aqueous-alkaline media, for the production of masks for screen printing, as dental filling compounds, as adhesives, as pressure-sensitive adhesives, as laminating resins, as etch or permanent resists and as solder masks for electronic circuits, in the manufacture of three-dimensional articles by bulk curing (UV curing in transparent moulds) or according to the stereolithography process, as described, for example, in U.S. Pat. No. 4,575,330, in the manufacture of composite materials (e.g. styrene polyesters which may include glass fibres and other adjuvants) and other thick-layered compositions, in the coating or sealing of electronic components or as coatings for optical fibres. The photoinitiator combinations according to the invention may also be used as initiators for emulsion polymerisation, as initiators of a polymerisation step for fixing orientation states of liquid-crystalline monomers and oligomers or as initiators for fixing dyes on organic materials.

In surface-coatings, use is frequently made of mixtures of a prepolymer with polyunsaturated monomers that also comprise a monounsaturated monomer, the prepolymer in particular determining the properties of the surface-coating film, so that a person skilled in the art will be able to influence the properties of the cured film by varying the prepolymer. The polyunsaturated monomer functions as a crosslinking agent, which renders the surface-coating film insoluble. The monounsaturated monomer functions as a reactive diluent, by means of which the viscosity is reduced without the need to use a solvent.

Unsaturated polyester resins are generally used in two-component systems together with a monounsaturated monomer, preferably styrene. For photoresists, specific one-component systems are often used, e.g. polymaleinimides, polychalcones or polyimides, as described in DE 2 308 830.

The photoinitiator combinations and compositions according to the invention can also be used, for example, in surface-coatings that are present in organic solvents and/or water or in solventless form.

The photoinitiator combinations according to the invention may also be used as photoinitiating systems for radiation-curable powder coating compositions. The powder coating compositions may be based on solid resins and monomers containing reactive double bonds, for example maleates, vinyl ethers, acrylates, acrylamides and mixtures thereof. A free-radically UV-curable powder coating composition may be formulated, for example, by mixing unsaturated polyester resins with solid acrylamides (e.g. methylacrylamidoglycolate methyl ester) and a free-radical photoinitiator combination according to the invention, as described, for example, in the presentation "Radiation Curing of Powder Coating", Conference Proceedings, Radtech Europe 1993 by M. Wittig and Th. Gohmann. Similarly, free-radically UV-curable powder coating compositions may be formulated by mixing unsaturated polyester resins with solid acrylates, methacrylates or vinyl ethers and a photoinitiator combination according to the invention. The powder coating compositions may also comprise binders, as described, for example, in DE 4 228 514 and EP 636 669. The UV-curable powder coating compositions may also comprise white or coloured pigments. For example, especially rutile/titanium dioxide may be used in concentrations of up to 50% by weight to obtain a cured powder coating composition having good hiding power. The process normally comprises spraying the powder electrostatically or tribostatically onto the substrate, for example metal or wood, melting the powder by heating and, after a smooth film has formed, radiation-curing the coating with ultraviolet and/or visible light, for example using medium-pressure mercury lamps, metal halide lamps or xenon lamps. A particular advantage of radiation-curable powder coating compositions over corresponding thermally curable compositions is that the flow time after the powder particles have been melted can be prolonged as desired in order to ensure the formation of a smooth high-gloss coating. Unlike thermally curable systems, radiation-curable powder coating compositions can be so formulated that they melt at relatively low temperatures without the undesired effect of their useful life being shortened. For that reason they are also suitable as coatings for heat-sensitive substrates, such as wood or plastics.

In addition to the photoinitiator combinations according to the invention the powder coating formulations may also comprise UV absorbers. Appropriate examples are listed hereinabove under points 1 to 8.

The photocurable compositions according to the invention are suitable, for example, as coating materials for all kinds of substrate, for example wood, textiles, paper, ceramics, glass, plastics, such as polyesters, polyethylene terephthalate, polyolefins and cellulose acetate, especially in the form of films, and also metals, such as Al, Cu, Ni, Fe, Zn, Mg or Co and GaAs, Si or $SiO_2$, to which a protective layer is to be applied or an image is to be applied by imagewise exposure.

The substrates; can be coated by applying a liquid composition, a solution or a suspension to the substrate. The choice of solvent and its concentration are governed chiefly by the nature of the composition and the coating method. The solvent should be inert, that is to say it should not enter into any chemical reaction with the components, and it should be capable of being removed again on drying after the coating operation. Suitable solvents include, for example, ketones, ethers and esters, such as methyl ethyl ketone, isobutyl methyl ketone, cyclopentanone, cyclohexanone, N-methylpyrrolidone, dioxane, tetrahydrofuran, 2-methoxy-ethanol, 2-ethoxyethanol, 1-methoxy-2-propanol, 1,2-dimethoxyethane, ethyl acetate, n-butyl acetate and ethyl 3-ethoxypropionate.

The solution is applied uniformly to a substrate by means of known coating methods, for example by spin-coating, immersion, knife coating, curtain pouring, brush application or spraying, especially by electrostatic spraying and reverse-roll coating. It is also possible to apply the photosensitive layer to a temporary flexible support and then coat the final substrate, e.g. a copper-clad circuit board, by transferring the layer by lamination.

The compositions according to the invention are preferably used in coatings, especially surface-coatings, e.g. white surface-coatings. The invention therefore relates also to a white surface-coating formulation comprising (A) at least one ethylenically unsaturated photopolymerisable compound, especially an acrylate;
(B) a photoinitiator combination as described above,
(C) optionally further photoinitiators,
(D) a white pigment, especially titanium dioxide, and optionally further additives.

The amount applied (layer thickness) and nature of the substrate (layer support) depend upon the desired field of use. The layer thickness range generally includes values of from approximately 0.1 μm to more than 10 mm.

The photosensitive compositions according to the invention are also used, for example, as negative resists that have a very high degree of photosensitivity and can be developed in an aqueous-alkaline medium without swelling. They are suitable as photoresists for electronics (galvanoresists, etch resists, solder resists), for the production of printing plates, such as offset printing plates or screen printing blocks, for use in the etching of mouldings or for use as microresists in the production of integrated circuits. The layer supports that are possible and the conditions for processing the coated substrates are correspondingly various.

For photographic information recordings there are used, for example, foils of polyester, cellulose acetate or plastics-coated papers; for offset printing blocks specially treated aluminium, for the production of printed circuits copper-clad laminates, and for the production of integrated circuits silicon wafers. The layer thicknesses for photographic materials and offset printing blocks are generally about from 0.5 μm to 10 mm, and for printed circuits from 0.4 μm to about 2 mm.

After the substrates have been coated, the solvent is generally removed by drying, resulting in a layer of the photoresist on the support.

The term "imagewise" exposure includes both exposure using a photomask having a predetermined pattern, e.g. a transparency, exposure using a laser beam which is moved over the surface of the coated substrate, for example under computer control, and in that way produces an image, and irradiation with computer-controlled electron beams.

After the imagewise exposure of the material and prior to development it may be advantageous to carry out a thermal treatment for a relatively short time. During the thermal treatment only the exposed areas are thermally cured. The temperatures used are generally from 50 to 150° C., preferably from 80 to 130° C.; the duration of the thermal treatment is generally from 0.25 to 10 minutes.

The photocurable composition may also be used in a method of producing printing blocks or photoresists, as described e.g. in DE 4 013 358. In such a method, before, at the same time as or after the imagewise irradiation the composition is exposed briefly to visible light of a wavelength of at least 400 nm without a mask.

After exposure and optional thermal treatment, the unexposed areas of the photosensitive coating are removed using a developer in a manner known per se.

As already mentioned, the compositions according to the invention can be developed in an aqueous-alkaline medium. Suitable aqueous-alkaline developer solutions are especially aqueous solutions of tetraalkylammonium hydroxides or of alkali metal silicates, phosphates, hydroxides and carbonates. If desired, relatively small amounts of wetting agents and/or organic solvents may be added to those solutions. Typical organic solvents that may be added in small amounts to the developer fluids are, for example, cyclohexanone, 2-ethoxy-ethanol, toluene, acetone and mixtures of such solvents.

Photocuring is of great importance for printing inks, since the drying time of the binder is a determining factor in the rate of production of graphic products and should be of the order of fractions of a second. UV-curable inks are important especially for screen printing.

The compositions according to the invention are also used especially for printing inks. The invention therefore relates also to a printing ink comprising a composition as described above or a photoinitiator combination according to the invention as described above. Acrylate-based printing inks are preferred.

As already mentioned above, the mixtures according to the invention are also very suitable for the production of printing plates. For that application there are used, for example, mixtures of soluble linear polyamides or styrene/butadiene or styrene/isoprene caoutchouc, polyacrylates or polymethyl-methacrylates having carboxyl groups, polyvinyl alcohols or urethane acrylates with polymerisable monomers, for example acrylic or methacrylic amides or acrylic or methacrylic esters, and a photoinitiator combination according to the invention. Films and plates made from those systems (wet or dry) are exposed through the negative (or positive) of the original and the uncured portions are then eluted with a suitable solvent.

Another field of use for photocuring is metal coating, for example in the application of a finish to sheets and tubes, cans or bottle closures, as well as photocuring on plastics coatings, for example of PVC-based floor or wall coverings.

Examples of the photocuring of paper coatings include the application of a colourless finish to labels, record sleeves or book covers.

Also of interest is the use of the photoinitiator combinations according to the invention in the curing of mouldings made of composite materials. The composite material consists of a self-supporting matrix material, for example woven glass fibres, or alternatively, for example, plant fibres [see K. -P. Mieck, T. Reussmann in Kunststoffe 85 (1995), 366–370], which is impregnated with the photocuring formulation. Mouldings made of composite materials that have been produced using the combinations according to the invention have a high degree of mechanical stability and resistance. The photoinitiator combinations according to the invention can also be used as photohardeners in moulding, impregnating and coating materials, as described, for example, in EP 7086. Such materials are, for example, thin-layer resins, on which high demands are made in terms of curing activity and resistance to yellowing, and fibre-reinforced moulding materials, such as planar or longitudinally or transversely corrugated light panels. Processes for the production of such moulding materials, such as, for example, manual lay-up processes, fibre-spraying, spinning or winding processes, are described, for example, by P. H. Selden in "Glasfaserverstärkte Kunststoffe", page 610, Springer Verlag Berlin-Heidelberg-New York 1967. Articles that can be produced, for example, according to that process are boats, chipboard or plywood panels coated on both sides with glass-fibre-reinforced plastics, pipes, containers etc. Further examples of moulding, impregnating and coating materials are UP resin thin layers for glass-fibre-containing moulding materials (GRP), for example corrugated panels and paper laminates. Paper laminates may be based on urea or melamine resins. The thin layer is produced on a support (for example a foil) prior to production of the laminate. The photocurable compositions according to the invention may also be used for casting-resins or for the potting of articles, for example electronic components etc. For curing, medium pressure mercury lamps are used, as are customary in UV curing, but less intense lamps, for example of the TL 40W/03 or TL40W/05 type, are also of particular interest. The intensity of those lamps roughly corresponds to that of sunlight. Direct sunlight can also be used for curing. A further advantage is that the composite material can be removed from the light source in a partially cured, plastic state and subjected to shaping, after which the full cure is effected.

Also important is the use of photocurable compositions for imaging processes and for the optical production of information carriers. For that application, as already described above, the layer (wet or dry) applied to the support is irradiated using a photomask with UV or visible light and the unexposed areas of the layer are removed by treatment with a solvent (=developer). The photocurable layer can also be applied to metal in an electrodeposition process. The exposed areas are crosslinked-polymeric and are therefore insoluble and remain on the support. When suitably coloured, visible images are formed. When the carrier is a metallised layer, after exposure and developing the metal can be etched away in the unexposed areas or strengthened by galvanisation. In this way it is possible to produce printed electronic circuits and photoresists.

The photosensitivity of the compositions according to the invention usually extends from the UV field (approximately 200 nm) to approximately 600 nm and therefore covers a very broad range. Suitable radiation is present, for example, in sunlight or light from artificial light sources. Accordingly a large number of the most varied kinds of light source may be used. Both point sources and planiform radiators (lamp carpets) are suitable. Examples are: carbon arc lamps, xenon arc lamps, medium pressure, high pressure and low pressure mercury arc radiators, doped, where appropriate, with metal halides (metal halide lamps), microwave-7excited metal vapour lamps, excimer lamps, superactinic fluorescent tubes, fluorescent lamps, argon incandescent lamps, electronic flash lamps, photographic floodlight lamps, electron beams and X-rays, produced by means of synchrotrons or laser plasma. The distance between the lamp and the substrate according to the invention to be exposed may vary according to the intended use and the type and strength of the lamp and may be, for example, from 2 cm to 150 cm. Especially suitable are laser light sources, for example excimer lasers, such as Krypton-F lasers for exposure at 248 nm. Lasers in the visible range may also be used.

The invention relates also to the use of the above-described composition in the production of surface-coatings, printing inks, printing plates, dental compounds, glass-fibre-containing moulding materials (GRP), casting compositions, resist materials and as image-recording material, especially for holographic recordings, and to a method of producing surface-coatings, printing inks, printing plates, dental compounds, glass-fibre-containing moulding materials (GRP), casting compositions, resist materials or image-recording material, especially for holographic recordings, wherein a composition as described above is applied to or mixed into such materials and irradiated with light in a wavelength range of from 200 to 600 nm.

The invention relates also to a coated substrate that is coated on at least one surface with a composition as described above, and to a method for the photographic production of relief images, wherein a coated substrate is exposed imagewise and then the unexposed portions are removed using a solvent.

In that procedure the imagewise exposure can be carried out as described above using a mask or alternatively with the aid of a controlled laser (without a mask).

The invention therefore relates also to a method for the photopolymerisation of compounds having ethylenically unsaturated double bonds, wherein a composition as described above is irradiated with light in a range of from 200 to 600 nm.

The photoinitiator combinations according to the invention exhibit good solubility in the substrates to be cured. When curing using the photoinitiator combinations according to the invention an optimum balance between the curing and the yellowing of the cured substrate can be achieved. The photoinitiator combinations are therefore reactive and low yellowing values can be obtained on curing.

The following Examples further illustrate the invention. Unless otherwise indicated, parts and percentages, both in the remainder of the description and in the patent claims, relate to weight.

EXAMPLE 1

Preparation of 2,4,6-trimethylbenzoyl-(2-methoxyethylphenyl)-phosphoric Acid Ester Oxide Under nitrogen, 20.0 g (0.109 mol) of 2,4,6-trimethylbenzoyl chloride are placed in 100 ml of toluene and heated to 80° C. 28.3 g (0.109 mol) of bis(2-methoxyethyl)-phenyl-phosphoric acid ester are added dropwise to the resulting solution at 80° C. over a period of 30 minutes. After being stirred at 80° C. for 2 hours, the yellow reaction solution is cooled to room temperature and the solvent is removed using a rotary evaporator. The residue is purified using a flash chromatography column (eluant:hexane/ethyl acetate 3:1). 28.9 g (76.6% of the theoretical yield) of the title compound are obtained in the form of a clear yellow oil. The signal in the $^{31}1'$-NMR spectrum appears at 18.92 ppm.

Elementary analysis: calculated: %C 65.32 found: %C 65.61 calculated: %H 07.50 found: %H 07.18

EXAMPLES 2–3

The compounds of Examples 2 and 3 are prepared by the same method as that described in Example 1 using the appropriate starting materials. The structures and physical data of the compounds are given in Table 1. The compounds are clear yellow oils in both cases.

TABLE 1

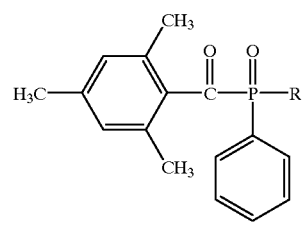

| | | | Elementary analysis [%] calc./found | |
|---|---|---|---|---|
| Example | R | $^{31}$P-NMR signal | H | C |
| 2 | —[O—(CH$_2$)$_2$]$_2$—O—CH$_3$ | 18.91 ppm | 8.01/7.24 | 66.83/64.36 |
| 3 | —[O—(CH$_2$)$_2$]$_3$—O—CH$_3$ | 18.78 ppm | 7.83/7.61 | 63.14/63.39 |

EXAMPLE 4

Preparation of bis(2,4,6-trimethylbenzoyl)phenylphosphine Oxide

With moisture being excluded by means of an argon atmosphere, at room temperature 7 g of lithium (1.0 mol; 25% excess) are suspended in 400 ml of tetrahydrofuran (THF), and 1.0 g (0.008 mol) of naphthalene is added. The mixture is stirred at room temperature for 10 minutes, yielding a dark-brown to black suspension. At 20–25° C. (occasional cooling with an ice-bath), with intensive stirring a solution of 36.50 g of P,P-dichlorophenylphosphine (98%; 0.20 mol) in 80 ml of THF is added dropwise over the course of one hour. With the exclusion of moisture and under argon protective gas, the black solution is filtered through a frit (G2 porosity) into a sulfonating flask. At room temperature, with stirring and cooling with an ice-bath, a solution of 80.4 g of 2,4,6-trimethylbenzoyl chloride (0.44 mol; 10% excess) in 250 ml of THF is added dropwise over a period of 1.5 hours and the mixture is then stirred at room temperature for 15 minutes. The organic phase is completely concentrated using a rotary evaporator (the resulting phosphine has a shift of 53.78 ppm in the $^{31}$P-NMR spectrum), the residue is taken up in 200 ml of toluene and heated to 40° C. With vigorous stirring and from time to time cooling with an ice-bath, 23 g of 30% hydrogen peroxide (0.20 mol) are added dropwise over a period of 30 minutes and then cooled to room temperature with stirring. 40 ml of water are added to the solution, the phases are separated and the organic phase is washed twice using 30 ml of 10% sodium hydrogen carbonate solution each time and then twice using 30 ml of water each time. Drying over magnesium sulfate, filtration and complete evaporation of the solvent yields 85 g of a yellow oil which becomes solid after drying for one hour at about 0.1 mbar. This crude product is purified by being made into a slurry in 150 ml of warm petroleum ether/ethyl acetate (9:1), filtering and washing with 30 ml of petroleum ether (40/60). 71.5 g (85.40% yield) of the title product are obtained in the form of a yellow solid having a melting point (m.p.) of 131–132° C. and a shift of 7.43 ppm in the $^{31}$P-NMR spectrum. From the mother liquor there are obtained by complete concentration of the solvent a further 14 g of the yellow oil, which is purified by flash chromatography and yields a further 4.3 g of the title product. The total yield is therefore 76.0 9 (90.8% yield).

EXAMPLE 5

Preparation and Curing of a White Surface-coating Formulation

A UV-curable white surface-coating is prepared by mixing together
67.5 parts poly(ester acrylate oligomer ($^{RTM}$EBECRYL 830, UCB, Belgium),
5.0 parts hexanediol diacrylate
2.5 parts trimethylolpropane triacrylate and
25.0 parts rutile titanium dioxide ($^{RTM}$R-TC2, Tioxide, France).

The photoinitiator mixtures to be tested are each incorporated into the formulation in a concentration of 2%.
The following photoinitiator mixtures are used:
P1 90% 2,4,6-trimethylbenzoyl-ethoxy-phenyl-phosphine oxide, 10% bis(2,4,6-trimethyl-benzoyl)phenyl-phosphine oxide,
P2 80% 2,4,6-trimethylbenzoyl-ethoxy-phenyl-phosphine oxide, 20% bis(2,4,6-trimethyl-benzoyl)phenyl-phosphine oxide,
P3 70% 2,4,6-trimethylbenzoyl-ethoxy-phenyl-phosphine oxide, 30% bis(2,4,6-trimethyl-benzoyl)phenyl-phosphine oxide.

The photoinitiator combinations are prepared by stirring the bisacylphosphine oxide component into the monoacylphosphine oxide component.

The surface-coating is applied with a 100 μm slotted knife to chipboard panels that have been coated with a white primer, is dried and then cured. The curing is in each case effected by conveying the sample on a conveyor belt, which is moving at a speed of 6 m/min, below two 80 W/cm medium pressure mercury lamps (AETEK apparatus). Thereafter the pendulum hardness according to König (DIN 53157) is determined in [s]. The pendulum hardness is a measure of the extent the composition has cured. The higher those values, the more effective is the result of the curing.

The results are shown in Table 2.

TABLE 2

| Photoinitiator | Pendulum hardness [s] |
|---|---|
| P1 | 136 |
| P2 | 149 |
| P3 | 159 |

EXAMPLE 6

Preparation and Curing of a White Surface-coating Formulation

A formulation is prepared as described in Example 5, but the photoinitiator combination is incorporated in a concentration of 3%. The following photoinitiator combination is used.
P4 15% bis(2,4,6-trimethylbenzoyl)phenyl-phosphine oxide, 7% 2,4,6-trimethylbenzoyl-ethoxy-phenyl-phosphine oxide, 78% 2-hydroxy-2-methyl-1-phenyl-propanone.

The formulation is applied and cured as described in Example 5, but the belt speed is 3 m/min. A pendulum hardness according to König of 175 s is obtained with photoinitiator combination 4.

EXAMPLE 7

Preparation and Curing of an Aqueous White Surface-coating Formulation

A UV-curable aqueous white surface-coating is prepared by mixing together
55.8% of a neutralised, monomer- and solvent-free, acrylic- and urethane-modified polyether ($^{RTM}$Viaktin VTE 6155w/50WA, from Vianova Resins, Austria),
10.2% water,
27.9% rutile titanium dioxide ($^{RTM}$Kronos 2310, from Kronos, Germany),
0.4% flow control agent ($^{RTM}$Byk 307, from Byk Chemie),
0.4% flow control agent ($^{RTM}$Byk 348, from Byk Chemie),
2.0% photoinitiator The following photoinitiator combinations are used:
P5 20% bis(2,4,6-trimethylbenzoyl)phenylphosphine oxide, 20% 2,4,6-trimethylbenzoyl-ethoxy-phenyl-phosphine oxide, 60% 2-hydroxy-2-methyl-1-phenyl-propanone
P6 10% bis(2,4,6-trimethylbenzoyl)phenylphosphine oxide, 30% 2,4,6-trimethylbenzoyl-ethoxy-phenyl-phosphine oxide, 60% 2-hydroxy-2-methyl-1-phenyl-propanone
P7 10% bis(2,4,6-trimethylbenzoyl)phenylphosphine oxide, 30% 2,4,6-trimethylbenzoyl-diphenyl-phosphine oxide, 60% 2-hydroxy-2-methyl-1-phenyl-propanone
P8 10% bis(2,4,6-trimethylbenzoyl)phenylphosphine oxide, 30% 2,4,6-trimethylbenzoyl-ethoxy-phenyl-phosphine oxide, 60% methylbenzoyl formate P9 10% bis(2,4,6-trimethylbenzoyl)phenylphosphine oxide, 30% 2,4,6-trimethylbenzoyl-ethoxy-phenyl-phosphine oxide, 60% of a mixture of 80 parts 2,4,6-trimethylbenzophenone and 20 parts 4-methylbenzophenone The surface-coating is applied with a 100 μm slotted knife to chipboard panels that have been coated with a white primer, is dried at 60° C. for 10 minutes and then cured. The curing is effected by conveying the sample on a conveyor belt, which is moving at a speed of 10 m/min, below two 80 W/cm medium pressure mercury lamps (AETEK apparatus). After curing, the pendulum hardness according to König (DIN 53157) is determined in [s]. The results are shown in Table 3.

TABLE 3

| Photoinitiator | Pendulum hardness [s] |
|---|---|
| P5 | 138 |
| P6 | 118 |
| P7 | 122 |
| P8 | 123 |
| P9 | 116 |

What is claimed is:

1. A photopolymerizable composition comprising
(A) at least one ethylenically unsaturated photopolymerizable compound, and
(B) a photoinitiator mixture which comprises
    (a) 5–50 wt.-% of at least one compound of formula I, based on 100 wt-% (I) and (II)

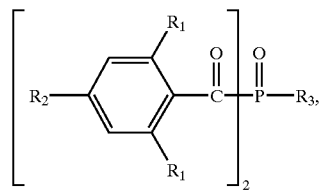

(I)

wherein
$R_1$ is $C_1$–$C_4$alkyl, $C_1$–$C_4$alkoxy or halogen;
$R_2$ is hydrogen, $C_1$–$C_4$alkyl, $C_1$–$C_4$alkoxy or halogen;
$R_3$ is $C_1$–$C_{20}$alkyl, cyclopentyl, cyclohexyl, phenyl-$C_1$–$C_4$alkyl or a group of formula (III)

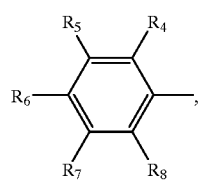

(III)

or $R_3$ is naphthyl, biphenylyl or an O-, S- or N-containing 5- or 6-membered heterocyclic ring, the naphthyl, biphenylyl and O-, S- or N-containing 5- or 6-membered heterocyclic ring radicals being unsubstituted or substituted by $C_1$–$C_4$alkyl, $C_1$–$C_4$alkoxy, halogen, $C_1$–$C_4$alkylthio;
$R_4$, $R_5$, $R_6$, $R_7$ and $R_8$ are each independently of the others hydrogen, halogen, $C_1$–$C_{20}$alkyl, cyclopentyl, cyclohexyl, $C_2$–$C_{21}$alkenyl, $C_2$–$C_{20}$alkyl interrupted by one or more non-consecutive O atoms, phenyl-$C_1$–$C_4$alkyl, $C_1$–$C_{20}$alkoxy, or phenyl that is unsubstituted or substituted by one or two $C_1$–$C_4$alkyl or/and $C_1$–$C_4$alkoxy substituents; and
    (b) 50–95 wt.-% of at least one compound of formula II based on 100 wt.-% (I) and (II)

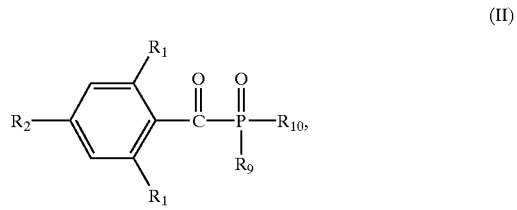

(II)

wherein
$R_1$ and $R_2$ are as defined above;
$R_9$ is $C_1$–$C_{20}$alkyl, cyclopentyl, cyclohexyl, phenyl-$C_1$–$C_4$alkyl, a group of formula (III), naphthyl, biphenylyl or an O-, S- or N-containing 5- or 6-membered heterocyclic ring, the naphthyl, biphenylyl and O-, S- or N-containing 5- or 6-membered heterocyclic ring radicals being unsubstituted or substituted by $C_1$–$C_4$alkyl, $C_1$–$C_4$alkoxy, halogen, $C_1$–$C_4$-alkylthio; and
$R_{10}$ is C, $C_{20}$alkyl, $C_2$–$C_{20}$alkyl interrupted by one or more non-consecutive O atoms, $C_1$–$C_{20}$alkoxy, cyclopentyl, cyclohexyl, phenyl-$C_1$–$C_4$alkyl, a group of formula (III), naphthyl, biphenylyl or an O-, S- or N-containing 5- or 6-membered heterocyclic ring, the naphthyl, biphenylyl and O-, S- or N-containing 5- or 6-membered heterocyclic ring radicals being unsubstituted or substituted by $C_1$–$C_4$alkyl, $C_1$–$C_4$alkoxy, halogen, $C_1$–$C_4$alkylthio.

2. A photopolymerizable composition according to claim 1 comprising in addition to component (B) also further initiators (C), additives (D) or mixture of (C) and (D).

3. A photopolymerizable composition according to claim 2 comprising as compoponent (D) a pigment and/or an ultraviolet absorber selected from the group consisting of hydrophenyl-s-triazines, hydroxyphenylbenzotriazoles, sterically hindered derivatives of 2,2,6,6-tetramethylpiperdines and mixtures thereof.

4. A composition according to claim 3 wherein the pigment of component (D) is a white pigment.

5. A method for the photopolymerization of compounds having ethylenically unsaturated double bonds, wherein a composition according to claim 1 is irradiated with light in a wavelength range of from 200 to 600 nm.

6. A method according to claim 5 for the production of surface-coatings, printing inks, printing plates, dental compounds, glass-fiber-containing molding materials (GRP), casting compositions, resist materials or image-recording materials, wherein a composition according to claim 1 is applied or mixed into such materials and irradiated with light in a wavelength range of from 200 to 600 nm.

7. A method according to claim 6 wherein the image-recording material is a holographic recording.

8. A white surface-coating formulation comprising
(A) at least one ethylenically unsaturated photopolymerizable compound;
(B) a photoinitiator combination described as component (B) according to claim 1;
(C) optionally further photoinitiators;

(D) a white pigment; and (E) optionally further additives.

9. A formulation according to claim 8 wherein component (A) is an acrylate.

10. A formulation according to claim 8 wherein the white pigment is titanium dioxide.

11. A coated substrate coated on at least one surface with a composition according to claim 1.

12. A coated substrated coated on at least one surface with a white surface-coating formulation according to claim 8.

13. A method for the photographic production of relief images wherein a substrate coated with a composition according to claim 1 is exposed imagewise and then the unexposed areas are removed using a solvent.

* * * * *